(12) United States Patent
Laing et al.

(10) Patent No.: US 8,372,592 B2
(45) Date of Patent: Feb. 12, 2013

(54) HIGH RESOLUTION LABEL FREE ANALYSIS OF CELLULAR PROPERTIES

(75) Inventors: Lance G. Laing, Belmont, MA (US); Rafael Fernandez, Jamaica Plain, MA (US); Rick Wagner, Cambridge, MA (US)

(73) Assignee: X-Body, Inc., Waltham, MA (US)

( * ) Notice: Subject to any disclaimer, the term of this patent is extended or adjusted under 35 U.S.C. 154(b) by 0 days.

(21) Appl. No.: 13/240,406

(22) Filed: Sep. 22, 2011

(65) Prior Publication Data

US 2012/0040866 A1   Feb. 16, 2012

Related U.S. Application Data

(63) Continuation of application No. 12/421,294, filed on Apr. 9, 2009.

(60) Provisional application No. 61/043,478, filed on Apr. 9, 2008.

(51) Int. Cl.
*G01N 33/53*   (2006.01)

(52) U.S. Cl. ............ 435/7.2; 435/7.21; 435/288.4; 435/288.7; 436/524; 436/525; 436/164; 436/805; 436/809; 422/407; 422/82.11

(58) Field of Classification Search .............. None
See application file for complete search history.

(56) References Cited

U.S. PATENT DOCUMENTS

| | | | |
|---|---|---|---|
| 3,689,346 A | 9/1972 | Rowland | |
| 3,810,688 A | 5/1974 | Ballman et al. | |
| 3,856,404 A | 12/1974 | Hershler et al. | |
| 3,916,182 A | 10/1975 | Dabby et al. | |
| 4,009,933 A | 3/1977 | Firester | |
| 4,050,895 A | 9/1977 | Hardy et al. | |
| 4,240,751 A | 12/1980 | Linnecke et al. | |
| 4,289,371 A | 9/1981 | Kramer | |
| 4,344,438 A | 8/1982 | Schultz | |
| 4,420,502 A | 12/1983 | Conley | |
| 4,536,608 A | 8/1985 | Sheng et al. | |
| 4,560,248 A | 12/1985 | Cramp et al. | |
| 4,576,850 A | 3/1986 | Martens | |
| 4,608,344 A | 8/1986 | Carter et al. | |
| 4,650,329 A | 3/1987 | Barrett et al. | |
| 4,652,290 A | 3/1987 | Cho et al. | |
| 4,668,558 A | 5/1987 | Barber | |
| 4,701,008 A | 10/1987 | Richard et al. | |
| 4,810,658 A | 3/1989 | Shanks et al. | |
| 4,815,843 A | 3/1989 | Tiefenthaler et al. | |
| 4,818,710 A | 4/1989 | Sutherland et al. | |
| 4,857,273 A | 8/1989 | Stewart | |
| RE33,064 E | 9/1989 | Carter | |
| 4,876,208 A | 10/1989 | Gustafson et al. | |

(Continued)

FOREIGN PATENT DOCUMENTS

| | | |
|---|---|---|
| CA | 2394966 | 8/2001 |
| CA | 2395318 | 8/2001 |

(Continued)

OTHER PUBLICATIONS

Patterson, "Proteomics: the Industrialization of protein chemistry", Current Opinions in Biotechnology, 11(4):413-8 (2000)*.

(Continued)

*Primary Examiner* — Chris L Chin
(74) *Attorney, Agent, or Firm* — McDonnell Boehnen Hulbert & Berghoff LLP

(57) ABSTRACT

The invention provides methods of detecting a change in cell growth patterns.

9 Claims, 3 Drawing Sheets

U.S. PATENT DOCUMENTS

| | | | |
|---|---|---|---|
| 4,882,288 | A | 11/1989 | North et al. |
| 4,888,260 | A | 12/1989 | Cowan |
| 4,931,384 | A | 6/1990 | Layton et al. |
| 4,952,056 | A | 8/1990 | Tiefenthaler |
| 4,958,895 | A | 9/1990 | Wells et al. |
| 4,992,385 | A | 2/1991 | Godfrey |
| 4,999,234 | A | 3/1991 | Cowen |
| 4,999,484 | A | 3/1991 | Kaneko |
| 5,071,248 | A | 12/1991 | Tiefenthaler et al. |
| 5,118,608 | A | 6/1992 | Layton et al. |
| 5,155,785 | A | 10/1992 | Holland et al. |
| 5,156,785 | A | 10/1992 | Zdrahala |
| 5,170,448 | A | 12/1992 | Ackley et al. |
| 5,175,030 | A | 12/1992 | Lu et al. |
| 5,210,404 | A | 5/1993 | Cush et al. |
| 5,216,680 | A | 6/1993 | Magnusson et al. |
| 5,229,614 | A | 7/1993 | Andersson et al. |
| 5,242,828 | A | 9/1993 | Bergstrom et al. |
| 5,268,782 | A | 12/1993 | Wenz et al. |
| 5,310,686 | A | 5/1994 | Sawyers et al. |
| 5,337,183 | A | 8/1994 | Rosenblatt |
| 5,416,884 | A | 5/1995 | Hirata et al. |
| 5,442,169 | A | 8/1995 | Kunz |
| 5,455,178 | A | 10/1995 | Fattinger |
| 5,475,780 | A | 12/1995 | Mizrahi |
| 5,478,527 | A | 12/1995 | Gustafson et al. |
| 5,478,756 | A | 12/1995 | Gizeli et al. |
| 5,492,840 | A | 2/1996 | Malmquist et al. |
| 5,496,701 | A | 3/1996 | Pollard-Knight |
| 5,559,338 | A | 9/1996 | Elliott et al. |
| 5,598,267 | A | 1/1997 | Sambles et al. |
| 5,598,300 | A | 1/1997 | Magnusson et al. |
| 5,601,997 | A | 2/1997 | Tchao |
| 5,606,170 | A | 2/1997 | Saaski et al. |
| 5,615,052 | A | 3/1997 | Doggett |
| 5,629,214 | A | 5/1997 | Crosby |
| 5,631,171 | A | 5/1997 | Sandstrom et al. |
| 5,666,197 | A | 9/1997 | Guerra |
| 5,690,894 | A | 11/1997 | Pinkel et al. |
| 5,691,846 | A | 11/1997 | Benson et al. |
| 5,732,173 | A | 3/1998 | Bylander et al. |
| 5,738,825 | A | 4/1998 | Rudigier et al. |
| 5,768,461 | A | 6/1998 | Svetkoff et al. |
| 5,771,328 | A | 6/1998 | Wortman et al. |
| 5,792,411 | A | 8/1998 | Morris et al. |
| 5,801,390 | A | 9/1998 | Shiraishi |
| 5,804,453 | A | 9/1998 | Chen |
| 5,814,516 | A | 9/1998 | Vo-Dinh |
| 5,814,524 | A | 9/1998 | Walt et al. |
| 5,821,343 | A | 10/1998 | Keogh |
| 5,864,641 | A | 1/1999 | Murphy et al. |
| 5,922,550 | A | 7/1999 | Everhart et al. |
| 5,925,878 | A | 7/1999 | Challener |
| 5,955,335 | A | 9/1999 | Thust et al. |
| 5,955,378 | A | 9/1999 | Challener |
| 5,955,729 | A | 9/1999 | Nelson |
| 5,986,762 | A | 11/1999 | Challener |
| 5,991,480 | A | 11/1999 | Kunz et al. |
| 5,994,150 | A | 11/1999 | Challener et al. |
| 5,998,298 | A | 12/1999 | Hetherington et al. |
| 6,035,089 | A | 3/2000 | Grann et al. |
| 6,042,998 | A | 3/2000 | Brueck et al. |
| 6,052,213 | A | 4/2000 | Burt et al. |
| 6,076,248 | A | 6/2000 | Hoopman et al. |
| 6,088,505 | A | 7/2000 | Hobbs |
| 6,100,991 | A | 8/2000 | Challener |
| 6,128,431 | A | 10/2000 | Siminovitch |
| 6,146,593 | A | 11/2000 | Pinkel et al. |
| 6,174,677 | B1 | 1/2001 | Vo-Dinh |
| 6,185,019 | B1 | 2/2001 | Hobbs et al. |
| 6,200,737 | B1 | 3/2001 | Walt et al. |
| 6,215,928 | B1 | 4/2001 | Friesem et al. |
| 6,218,194 | B1 | 4/2001 | Lyndin et al. |
| 6,235,488 | B1 | 5/2001 | Tom-Moy et al. |
| 6,277,653 | B1 | 8/2001 | Challener |
| 6,303,179 | B1 | 10/2001 | Koulik et al. |
| 6,316,153 | B1 | 11/2001 | Goodman et al. |
| 6,320,991 | B1 | 11/2001 | Challener et al. |
| RE37,473 | E | 12/2001 | Challener |
| 6,332,663 | B1 | 12/2001 | Puzio et al. |
| 6,338,968 | B1 | 1/2002 | Hefti |
| 6,340,598 | B1 | 1/2002 | Herron et al. |
| 6,346,376 | B1 | 2/2002 | Sigrist et al. |
| 6,377,721 | B1 | 4/2002 | Walt et al. |
| 6,395,558 | B1 | 5/2002 | Duveneck et al. |
| 6,404,554 | B1 | 6/2002 | Lee et al. |
| 6,449,097 | B1 | 9/2002 | Zhu et al. |
| 6,558,957 | B1 | 5/2003 | Roinestad et al. |
| 6,570,657 | B1 | 5/2003 | Hoppe et al. |
| 6,579,673 | B2 | 6/2003 | McGrath et al. |
| 6,587,276 | B2 | 7/2003 | Daniell |
| 6,661,952 | B2 | 12/2003 | Simpson et al. |
| 6,707,561 | B1 | 3/2004 | Budach et al. |
| 6,748,138 | B2 | 6/2004 | Wang et al. |
| 6,771,376 | B2 | 8/2004 | Budach et al. |
| 6,867,869 | B2 | 3/2005 | Budach et al. |
| 6,870,624 | B2 | 3/2005 | Hobbs et al. |
| 6,870,630 | B2 | 3/2005 | Budach et al. |
| 6,902,703 | B2 | 6/2005 | Marquiss et al. |
| 6,951,715 | B2 | 10/2005 | Cunningham |
| 6,982,171 | B2 | 1/2006 | Kim |
| 6,990,259 | B2 | 1/2006 | Cunningham |
| 7,018,838 | B2 | 3/2006 | Murphy |
| 7,023,544 | B2 | 4/2006 | Cunningham |
| 7,033,819 | B2 | 4/2006 | Kim |
| 7,033,821 | B2 | 4/2006 | Kim |
| 7,064,844 | B2 | 6/2006 | Budach et al. |
| 7,070,987 | B2 | 7/2006 | Cunningham |
| 7,074,311 | B1 | 7/2006 | Cunningham |
| 7,094,595 | B2 | 8/2006 | Cunningham |
| 7,101,660 | B2 | 9/2006 | Cunningham et al. |
| 7,118,710 | B2 | 10/2006 | Cunningham |
| 7,142,296 | B2 | 11/2006 | Cunningham et al. |
| 7,148,964 | B2 | 12/2006 | Cunningham et al. |
| 7,153,702 | B2 | 12/2006 | Lin |
| 7,158,230 | B2 | 1/2007 | Cunningham et al. |
| 7,162,125 | B1 | 1/2007 | Schulz |
| 7,170,599 | B2 | 1/2007 | Cunningham et al. |
| 7,175,980 | B2 | 2/2007 | Qiu et al. |
| 7,197,198 | B2 | 3/2007 | Schulz et al. |
| 7,202,076 | B2 | 4/2007 | Cunningham et al. |
| 7,217,574 | B2 | 5/2007 | Pien et al. |
| 7,264,973 | B2 | 9/2007 | Lin et al. |
| 7,267,993 | B2 | 9/2007 | Pentrenko |
| 7,292,336 | B2 | 11/2007 | Cunningham et al. |
| 7,298,477 | B1 | 11/2007 | Cunningham et al. |
| 7,300,803 | B2 | 11/2007 | Lin et al. |
| 7,301,628 | B2 | 11/2007 | Cunningham et al. |
| 7,306,827 | B2 | 12/2007 | Li et al. |
| 7,309,614 | B1 | 12/2007 | Baird |
| 7,312,090 | B2 | 12/2007 | Lin et al. |
| 7,327,454 | B2 | 2/2008 | Cunningham et al. |
| 7,396,675 | B2 | 7/2008 | Pawlak et al. |
| 7,400,399 | B2 | 7/2008 | Cunningham et al. |
| 7,479,404 | B2 | 1/2009 | Cunningham |
| 7,483,127 | B1 | 1/2009 | Li |
| 7,497,992 | B2 | 3/2009 | Cunningham |
| 7,521,769 | B2 | 4/2009 | Cunningham |
| 7,524,625 | B2 | 4/2009 | Madison |
| 7,534,578 | B1 | 5/2009 | Baird |
| 7,620,276 | B2 | 11/2009 | Schulz |
| 7,628,085 | B2 | 12/2009 | Laing |
| 7,742,662 | B2 | 6/2010 | Cunningham |
| 7,756,365 | B2 | 7/2010 | Cunningham |
| 7,790,406 | B2 | 9/2010 | Cunningham |
| 2002/0018610 | A1 | 2/2002 | Challener et al. |
| 2002/0028045 | A1 | 3/2002 | Yoshimura |
| 2002/0028480 | A1 | 3/2002 | Maher |
| 2002/0123050 | A1 | 9/2002 | Poponin |
| 2002/0127565 | A1 | 9/2002 | Cunningham et al. |
| 2002/0135752 | A1 | 9/2002 | Sokolov et al. |
| 2002/0171045 | A1 | 11/2002 | Perraut |
| 2003/0003599 | A1 | 1/2003 | Wagner et al. |
| 2003/0017580 | A1 | 1/2003 | Cunningham |
| 2003/0017581 | A1 | 1/2003 | Li |
| 2003/0026891 | A1 | 2/2003 | Qiu |
| 2003/0027327 | A1 | 2/2003 | Cunningham et al. |

| | | |
|---|---|---|
| 2003/0027328 A1 | 2/2003 | Cunningham et al. |
| 2003/0032039 A1 | 2/2003 | Cunningham |
| 2003/0059855 A1 | 3/2003 | Cunningham |
| 2003/0068657 A1 | 4/2003 | Lin |
| 2003/0077660 A1 | 4/2003 | Pien |
| 2003/0092075 A1 | 5/2003 | Pepper |
| 2003/0104479 A1 | 6/2003 | Bright |
| 2003/0108954 A1 | 6/2003 | Mutz |
| 2003/0113766 A1 | 6/2003 | Pepper |
| 2003/0148542 A1 | 8/2003 | Pawlak |
| 2003/0210396 A1 | 11/2003 | Hobbs et al. |
| 2003/0224369 A1 | 12/2003 | Surber et al. |
| 2004/0005540 A1 | 1/2004 | Petrenko |
| 2004/0011965 A1 | 1/2004 | Hodgkinson |
| 2004/0091397 A1 | 5/2004 | Picard |
| 2004/0132172 A1 | 7/2004 | Cunningham |
| 2004/0132214 A1 | 7/2004 | Lin |
| 2004/0151626 A1 | 8/2004 | Cunningham |
| 2004/0191757 A1 | 9/2004 | Maher |
| 2004/0219619 A1 | 11/2004 | Fernandez-Salas |
| 2005/0058639 A1 | 3/2005 | Gudas |
| 2005/0074825 A1 | 4/2005 | Luo |
| 2005/0214803 A1 | 9/2005 | Wang |
| 2005/0221271 A1 | 10/2005 | Murphy |
| 2005/0227374 A1 | 10/2005 | Cunningham et al. |
| 2006/0003372 A1 | 1/2006 | Li |
| 2006/0030033 A1 | 2/2006 | Cunningham |
| 2006/0040376 A1 | 2/2006 | Cunningham et al. |
| 2006/0057707 A1 | 3/2006 | Lin et al. |
| 2006/0181705 A1 | 8/2006 | Cunningham |
| 2006/0193550 A1 | 8/2006 | Wawro et al. |
| 2006/0275825 A1 | 12/2006 | Laing et al. |
| 2006/0281077 A1 | 12/2006 | Lin |
| 2006/0286663 A1 | 12/2006 | Cunningham et al. |
| 2007/0015210 A1 | 1/2007 | Ezekiel |
| 2007/0041012 A1 | 2/2007 | Cunningham et al. |
| 2007/0054339 A1 | 3/2007 | Lin |
| 2007/0070355 A1 | 3/2007 | Cunningham et al. |
| 2007/0141231 A1 | 6/2007 | Cunningham et al. |
| 2007/0172894 A1 | 7/2007 | Genick et al. |
| 2008/0213910 A1 | 9/2008 | Jogikalmath |
| 2008/0219892 A1 | 9/2008 | Cunningham |
| 2008/0240543 A1 | 10/2008 | Budach |
| 2008/0299673 A1 | 12/2008 | Wagner |
| 2009/0130703 A1 | 5/2009 | Wagner |
| 2009/0137422 A1 | 5/2009 | Laing |
| 2009/0148955 A1 | 6/2009 | Cunningham |
| 2009/0176658 A1 | 7/2009 | Madison |
| 2009/0179637 A1 | 7/2009 | Cunningham |
| 2009/0192049 A1 | 7/2009 | Baird |
| 2009/0227469 A1 | 9/2009 | Conklin |
| 2009/0264314 A1 | 10/2009 | Cunningham |
| 2009/0269244 A1 | 10/2009 | Cunningham |
| 2009/0282931 A1 | 11/2009 | Laing |
| 2009/0305304 A1 | 12/2009 | Laing |
| 2010/0003743 A1 | 1/2010 | Schulz |
| 2010/0008826 A1 | 1/2010 | Schulz |
| 2010/0015721 A1 | 1/2010 | Laing |
| 2010/0043571 A1 | 2/2010 | Laing |
| 2010/0143959 A1 | 6/2010 | Cunningham |
| 2010/0195099 A1 | 8/2010 | Rockney |
| 2010/0196925 A1 | 8/2010 | Genick |
| 2010/0202923 A1 | 8/2010 | Cunningham |
| 2010/0227769 A1 | 9/2010 | Schulz |
| 2010/0231907 A1 | 9/2010 | Pien |
| 2010/0291575 A1 | 11/2010 | Shamah |

FOREIGN PATENT DOCUMENTS

| | | |
|---|---|---|
| CH | 669050 | 2/1989 |
| CH | 670521 | 6/1989 |
| EP | 0075353 | 3/1983 |
| EP | 0112721 | 7/1984 |
| EP | 0326219 | 1/1989 |
| EP | 0517777 | 5/1996 |
| EP | 0660924 | 9/1999 |
| EP | 1031828 | 8/2000 |
| EP | 1085315 | 3/2001 |
| FR | 2801977 | 12/1999 |
| GB | 2156970 | 10/1985 |
| GB | 2227089 | 7/1990 |
| JP | 1993228946 | 9/1993 |
| WO | 81/00912 | 2/1981 |
| WO | 84/02578 | 7/1984 |
| WO | 86/07149 | 12/1986 |
| WO | 90/08313 | 7/1990 |
| WO | 91/13339 | 9/1991 |
| WO | 92/04653 | 3/1992 |
| WO | 92/21768 | 12/1992 |
| WO | 93/17392 | 7/1993 |
| WO | 95/03538 | 2/1995 |
| WO | 96/38726 | 5/1996 |
| WO | 97/29362 | 8/1997 |
| WO | 9837147 | 2/1998 |
| WO | 98/10288 | 3/1998 |
| WO | 98/57200 | 12/1998 |
| WO | 99/09369 | 2/1999 |
| WO | 99/09392 | 2/1999 |
| WO | 99/54714 | 10/1999 |
| WO | 99/66330 | 12/1999 |
| WO | 00/23793 | 4/2000 |
| WO | 00/29830 | 5/2000 |
| WO | 01/02839 | 1/2001 |
| WO | 01/04697 | 1/2001 |
| WO | 01/79559 | 10/2001 |
| WO | 01/92870 | 12/2001 |
| WO | 02/061429 | 8/2002 |
| WO | 03074548 | 9/2003 |
| WO | 2007064702 | 6/2007 |
| WO | 2009009718 | 1/2009 |
| WO | 2010005600 | 1/2010 |
| WO | 2010075033 | 7/2010 |

OTHER PUBLICATIONS

Peng et al., "Experimental demonstration of resonant anomalies in diffraction from two-dimensional gratings", Optics Letters, vol. 21, No. 8, pp. 549-551 (1996)*.
Peng et al., "Resonant scattering from two-dimensional gratings", J. Opt. Soc. Am. A., vol. 13, No. 5, pp. 993-1005 (1996)*.
Raguin et al., "Structured Surfaces Mimic Coating Performance", Laser Focus World, pp. 113-117 (1997)*.
Sigal et al., "A Self-Assembled Monolayer for the Binding and Study of Histidine-Tagged Proteins by Surface Plasmon Resonance", Analytical Chemistry, vol. 68, No. 3, pp. 490-497 (1996)*.
Wang et al., "Design of waveguide-grating filters with symmetrical line shapes and low sidebands", Optical Society of America, vol. 19, No. 12, pp. 919-921 (1994)*.
Wang et al., "Guided-mode resonances in planar dielectric-layer diffraction gratings", J. Opt. Soc. Am., vol. 7, No. 8, pp. 1470-1474 (1990)*.
Wang et al., "Theory and applications of guided-mode resonance filter", Applied Optics, vol. 32, No. 14, pp. 2606-2613 (1993)*.
International Search Report for foreign counterpart application PCT/US01/50723, Sep. 17, 2002*.
International Search Report for foreign counterpart application PCT/US03/01175, Aug. 18, 2003*.
Invitation to Pay Additional Fees in foreign counterpart application PCT/US01/50723, Aug. 30, 2002*.
Haidner, "Zero-Order Gratings Used as an Artificial Distributed Index Medium", Optik, Wissenschaftliche Verlag GmbH, Stuttgart, DE, vol. 89, No. 3, pp. 107-112 (1992)*.
Wilson et al., "The Optical Properties 1-19 of 'Moth Eye' Antireflection Surfaces", Optica ACTA, vol. 29, No. 7, pp. 993-1009 (1982)*.
Bagnich et al., "Tunable Optical Filter", Derwent Publications, English Translation, Abstract Only,Derwent Publications Ltd. (Mar. 15, 1989)*.
*Corning Inc.* v. *SRU Biosystems, Inc.*, Memorandum Opinion dated Nov. 15, 2005 in the United States District Court for the district of Delaware*.
Liu et al., "Development of an optical fiber lactate sensor", Mikrochimica Acta, 131(1-2), pp. 129-135 (1999)*.
U.S. Appl. No. 11/635,934, filed Dec. 8, 2006*.
U.S. Appl. No. 11/566,818, filed Dec. 5, 2006*.
U.S. Appl. No. 11/506,639, filed Aug. 18, 2007*.
U.S. Appl. No. 11/749,079, filed May 15, 2007*.

U.S. Appl. No. 11/828,076, filed Jul. 25, 2007*.

European Search Report for EP 07 11 8355 dated Feb. 5, 2008*.

Nelson, et al., "BIA/MS of Epitope-Tagged Peptides Directly from *E. coli* Lysate: Multiplex Detection and Protein Identification at Low-Femtomole to Subfemtomole Levels", Anal. Chem. 1999, 71, 2858-2865*.

Moffatt, "Optical probes May Hasten Shift of Diagnostics from Lab to Doc's Office", Genetic Engineering News, vol. 18, (1986), p. 18*.

Williams, et al., "The integration of SPR biosensors with mass spectrometry: possible applications for proteome analysis", Trends in Microbiology, Elsevier, vol. 18, No. 2 (2000) pp. 45-48*.

Cekaite et al., "Analysis of the humoral immune response to immunoselected phage-displayed peptides by a microarray-based method", Proteomics 2004, 4, 2572-2582*.

Sun et al., "Use of bioluminescent Salmonella for assessing the efficiency of constructed phage-based biosorbent", Journal of Industrial Microbiology & Biotechnology, 2000, 25, 273-275*.

Wan, et al., "Landscape phage-based magnetostrictive biosensor for detecting *Bacillus anthracis* spores", Proc. IEEE Sens., 2005, 1308-1311*.

Cunningham, et al., "Label-Free Assays on the BIND System", Journal of Biomolecular Screening, vol. 9, p. 481-490 (2004)*.

Cunningham, "Label-Free Detection with the Bind System", Presented at Screentech General, Mar. 24, 2003*.

Baird, "Beyond ELISA's: Label-free Detectionw ith BIND", Presented at Interphex Meeting in Europe, Mar. 16-18, 2004*.

Cunningham, et al., "Colorimetric Resonant Reflection as a Direct Biochemical Assay Technique", Presented at the Pittsburgh Conference and Exposition on Analytical Chemistry and Applied Spectroscopy, Morial Convention Center in New Orleans, LA Mar. 17-22, 2002*.

Broad et al., "Growth and adipose differentiation of sheep preadipocyte fibroblasts in serum-free medium", Eur. J. Biochem., 135, 33-39 (1983)*.

Castillo et al., "Characterization of proliferation and differentiation of EGF-response striatal and septal precursor cells", Int. J. Devl. Neuroscience 21 (2003) 41-47*.

Chalazonitis, et al., "The a1 Subunit of Laminin-1 Promotes the Development of Neurons by Interacting with LBP110 Expressed by Neural Crest-Derived Cells Immunoselected from the Fetal Mouse Gut", J. Neurobiol. 33:118-138, 1997*.

Hao et al., "Fetal Human Hemotopoietic Stem Cells Can Differentiate Sequentially into Neural Stem Cells and then Astrocytes in Vitro", Journal of Hematotherapy & Stem Cell Research, 12:23-32 (2003)*.

Kano, et al "Establishment of Hepatic Stem-like Cell Lines from Normal Adult Porcine Liver in a Poly-D-Lysine-Coated . Dish with Nair-1 Medium", In Vitro Cell. Dev. Biol. Animal, 30-440-448 (2003)*.

Sung, et al., "Adhesiveness of Human Ligament Fibroblasts to Laminin", Journal of Orthopaedic Research, 13:166-173 (1995)*.

Zhou, et al., "Long-term nonpassaged EGF-responsive neural precursor cells are stem cells", Wound Repair and Regeneration, vol. 6, No. 4, pp. 337-348, 1998*.

Adamczyk, et al., "Application of Surface Plasmon Resonance toward Studies of Low-Molecular-Weight Antigen-Antibody Binding Interactions", Methods, 20, pp. 319-328 (2000)*.

Marquart, "Immobilization Techniques", SPR pp. [online] Jan. 2004, pp. 1-7*.

Zhang, et al., "Use of surface plasmon resonance for the measurement of low affinity binding interactions between HSP72 and measles virus nucleocapsid protein", Biol. Proced. Online 2003;5(1):170-181*.

Gestwicki, et al., "Using Receptor Conformational Change to Detect Low Molecular Weight Analytes by Surface Plasmon Resonance", Anal. Chem., 2001, 4, 5732-5737*.

International Search Report dated Jul. 15, 2008, for PCT application serial No. PCT/US08/60951*.

English machine translation only of JP 1993-228946 Sep. 7, 1993*.

U.S. Appl. No. 12/171,475, filed Jul. 11, 2008*.

U.S. Appl. No. 12/335,393, filed Dec. 15, 2008*.

International Search Report for corresponding application No. PCT/US09/30412 dated Jan. 8, 2009*.

Wawro, et al., "Optical fiber endface biosensor based on resonances in dielectric waveguide gratings", Biomedical Diagnostic Guidance and Surgical-Assist Systems II, Vo-Dihn et al eds., Proceedings of SPIE, vol. 3911, p. 86-94 (2000)*.

Office action dated Apr. 2, 2007, for U.S. Appl. No. 11/506,639 (now U.S. Patent No. 7,298,477)*.

Brecht et al., "Optical probes and transducers", Biosensors & Bioelectronics, vol. 10, pp. 923-936 (1995)*.

Challener et al., "A multilayer grating-based evanescent wave sensing technique", Sensors and Actuators B, 71, pp. 42-46 (2000)*.

Cowan, "Aztec surface-relief volume diffractive structure", J. Opt. Soc. Am. vol. 7, No. 8, pp. 1529-1544 (1990)*.

Cowan, "Holographic honeycomb microlens", Optical Engineering, vol. 24, No. 5, pp. 796-802 (1985)*.

Cowan, "The Recording and Large Scale Replication of Crossed Holographic Grating Arrays using Multiple Beam Interferometry", SPIE, vol. 503, Application, Theory, and Fabrication of Periodic Structures, pp. 120-129 (1984)*.

Cowan et al., "The Recording and Replication of Holographic Micropatterns for the Ordering of Photographic Emulsion Grains in Film Systems", J. Imaging Sci., vol. 31, No. 3, pp. 100-107 (1987)*.

Introduction to Bioanalytical Sensors (Techniques in Analytical Chemistry) (Cunningham ed., 1988) pp. 260-291, "Optical Based Energy Transduction", Wiley Interscience, Hoboken, NJ*.

Hobbs et al., "Automated Interference Lithography Systems for Genereation of Sub-Micron Feature Size Patterns", SPIE, vol. 3879, pp. 124-135 (1999)*.

Huber et al., "Direct optical immunosensing (sensitivity and selectivity)", Sensors and Actuators B, 6, pp. 122-126 (1992)*.

Jenison et al., "Interference-based detection of nucleic acid targets on optically coated silicon", Nature Biotechnology, vol. 19, pp. 62-64 (2001)*.

Jin et al., "A biosensor concept based on imaging ellipsometry for visualization of biomolecular interactions", Analytical Biochemistry, vol. 232, pp. 69-72 (1995)*.

Jordan et al., "Surface Plasmon Resonance Imaging Measurements of Electrostatic Biopolymer Adsorption onto Chemically Modified Gold Surfaces", Analytical Chemistry, vol. 69, No. 7, pp. 1449-1456 (1997)*.

Lin et al., A Porous Silicon-Based Optical Interferometric Biosensor:, Science, vol. 278, pp. 840-843 (1997)*.

Magnusson et al., "New principle for optical filters", Appl. Phys. Lett., vol. 61, No. 9, pp. 1022-1024 (1992)*.

Magnusson et al., "Transmission bandpass guided-mode resonance filters", Applied. Optics, vol. 34, No. 35, pp. 8106-8109 (1995)*.

Morhard et al., "Immobilization of antibodies in micropatterns for cell detection by optical diffraction", Sensors and Actuators B, 70, pp. 232-242 (2000)*.

Pandey et al, "Proteomics to study genes and genomes", Natures 405(6788):837-46 (2000)*.

Patel et al., "Electrically tuned and polarization insensitive Fabry-Perot etalon with a liquid-crysatl film", App. Phys. Lett., vol. 58, No. 22, pp. 2491-2493 (1993)*.

Bertoni et al., "Frequency-Selective Reflection and Transmission by a Periodic Dielectric Layer", IEEE Transaction on Antennas and Propagation, vol. 37, No. 1, pp. 78-83 (1989)*.

Brundrett et al., "Normal-incidence guided-mode resonant grating filters: design and experimental demonstration", Optics Letters, vol. 23, No. 9, pp. 700-702 (1998)*.

Peng "Polarization-control Components and Narrow-band Filters Based on Subwavelength Grating Structures", 1996*.

Statement of Applicants dated May 10, 2004*.

Leanu, Torben, Material, Silicon Nitride, 1996, 97, 98*.

Cerac, Technical publications: Tantalum Oxide, Ta2O5 for Optical Coating, 2000, Cerac, Inc*.

Neuschafer et al., Evanescent resonator chips: a universal platform with superior sensitivity for fluorescence-based microarrays, Biosensors & Bioelectronics, 18, pp. 489-497 (2003)*.

Budach et al., "Generation of transducers for fluorescence-based microarrays with enhanced sensitivity and their application for gene expression profiling", Analytical Chemistry, 1;75(11):2571-7 (2003)*.

Anderson et al., "Proteomics: applications in basic and applied biology", Current Opinion in Biotechnology, 11:408-412 (2000)*.
MacBeath et al., "Printing Proteins as Microarrays for High-Throughput Function Determination", Science, vol. 289, pp. 1760-1763 (2000)*.
deWildt et al, "Antibody arrays for high-throughput screening of antibody-antigen interactions", Nature Biotechnology, vol. 18, pp. 989-994 (2000)*.
Cunningham et al., "A plastic colorimetric resonant optical biosensor for multiparallel detection of label-free biochemical interactions" Sensors and Actuators B, 85, pp. 219-226 (2002)*.
Caruso et al., "Quartz Crystal Microbalance Study of DNA Immobilization and Hybridization for Nucleic Acid Sensor Development", Analytical Chemistry, vol. 69, No. 11, pp. 2043-2049 (1997)*.
Hefti et al., "Sensitive detection method of dielectric dispersions in aqueous-based, surface-bound macromolecular structures using microwave spectroscopy", Applied Physics Letters, vol. 75, No. 12, pp. 1802-1084 (1999)*.
Wu et al., "Bioassay of prostate-specific antigen (PSA) using microcantilevers", Nature Biotechnology, vol. 19, pp. 856-860 (2001)*.
Wasserman et al., "Structure and Reactivity of Alkylsiloxane Monolayers Formed by Reaction of Alkyltrichlorosilanes on Silicone Substrates", Langmuir, 5, pp. 1074-1087 (1989)*.
Kallury et al., "X-ray Photoelectron Spectroscopy of Silica Surfaces Treated with Polyfunctional Silanes", Anal. Chem. 60, 169-172 (1988)*.
Cunningham et al., "Colorimetric resonant reflection as a direct biochemical assay technique", Sensors and Actuators B, 81 (2002) 316-328*.
Mullaney et al, "Epitope Mapping of Neutralizing Botulinum Neurotoxin A Antibodies by Phage Display", Infection and Immunity, vol. 69, No. 10, pp. 6511-6514 (2001)*.
Nellen et al., "Integrated Optical Input Grating Couplers as Biochemical Sensors", Sensors and Actuators, 15 (1988) 285-295*.
Lukosz and Tiefenthaler, "Embossing technique for fabricating integrated optical components in hard inorganic waveguiding materials", Optics Letters vol. 8, pp. 537-539 (1983)*.
Tiefenthaler and Lukosz, "Integrated optical switches and gas sensors", Optics Letters, vol. 10, pp. 137-139 (1984)*.
Chabay, "Optical Waveguides", Analytical Chemistry, vol. 54, pp. 1071A-1081A (1982)*.
Sutherland et al., "Optical Detection of Antibody-antigen Reactions at a Glass-Liquid Interface", Clin. Chem. vol. 30, pp. 1533-1538 (1984)*.
Holm and Palik, "Internal-reflection spectroscopy", Laser Focus, vol. 15, pp. 60-65 (1979)*.
Harrick and Loeb, "Multiple Internal Reflection Fluorescence Spectrometry", Analytical Chemistry, vol. 45, pp. 687-691 (1973)*.
Tien, "Light Waves in This Films and Integrated Optics", Applied Optics, vol. 10, pp. 2395-2413 (1971)*.
Dakss et al., "Grating Coupler for Efficient Excitation of Optical Guided Waves in Thin Films", Applied Physics Letters, vol. 16, pp. 523-525 (1970)*.
Sutherland et al., "Immunoassays at a Quartz-Liquid Interface: Theory, Instrumentation and Preliminary Application to Fluorescent Immunoassay of Human Immunoglobulin G", Journal of Immunological Methods, vol. 74, pp. 253-265 (1984)*.
English Translation of CH 670 521 A5 (Jun. 15, 1989), translation dated Oct. 29, 2003*.
English Translation of CH 669 050 A5 (Feb. 15, 1989), translation dated Oct. 29, 2003*.
Patel et al., "Multi-Wavelength Tunable Liquid-Crystal Etalon Filter", IEEE Photonics Technology Letters, vol. 3, No. 7, pp. 643-644 (1991)*.
Torbin, et al., "The use of polymerizing cements for making replicas of optical surfaces", Optical Technology, vol. 40, No. 3, p. 192-196 (1973)*.
Ramsden, et al., "Optical Method for Measurement of Number and Shape of Attached Cells in Real Time", Cytometry, vol. 19, pp. 97-102 (1995)*.
Li et al., "Measurement and Adhesion and Spreading Kinetics of Baby Hamster Kidney and Hybridoma Cells Using an Integrated Optical Method", Biotechnol. Prog., vol. 10, pp. 520-524 (1994)*.
International Search Report dated Jul. 2, 2010, for corresponding PCT application No. PCT/US2010/035152, filed May 17, 2010*.
Cunningham et al., "Advantages and application of label-free detection assays in drug screening", Expert Opin. Drug Discov., 3(7):891-901 (2008)*.
Palmer, "Diffraction Gratings, The Crucial Dispersive Component", Spectroscopy, 10(2), pp. 14-15 (1995)*.
Bandell et al., "Noxious Cold Ion Channel TRPA1 is Activated by Pungent Compounds and Bradykinin" Neuron, vol. 41, pp. 849-957 (2004)*.
Cunningham et al., "Label-Free Assays on the BIND System", Journal of Biomolecular Screening, 9:481 (2004)*.
Imt Applied Optics, "Resonant Grating Filters", 2008*.
Cunningham et al., "Advantages and application of label-free detection assays in drug screening", Expert Opin. Drug Discovery, 3:891-901 (2008)*.
Comley, "Label-Free Detection New biosensors facilitate boarder range of drug discovery applications", Drug Discovery World Winter, p. 63-74 (May 2004)*.
Cooper, "Current biosensor technologies in drug discovery", Drug Discovery World Summer, p. 68-82 (2006)*.
Cunningham et al., "Colormetric Resonant Reflection as a Direct Biochemical Assay Technique", IEEE, Annual International Conference on Micro Electro Mechanical Systems, MEMS, Las Vegas, NV, Jan. 20-24, 2002*.
Cunningham et al., "Label-Free Assays on the BIND System", Journal of Biomolecular Screening 9(6):481-490 (2004)*.
Magnusson et al., "Fiber Endface Bioprobes with high Sensitivity and Spatial Resolution", Grant Proposal dated Aug. 11, 1999*.
Norton, "Resonant Grating Structures: Theory, Design and Applications", Doctoral Thesis, The University of Rochester, 1997*.
Popov et al., "Theoretical study of the anomalies of coated dielectric gratings", Optica Acta, vol. 33, No. 5, pp. 607-619 (1986)*.
Shin et al., "Thin-film optical filters with diffractive elements and waveguides", Opt. Eng. 37(9):2634-2646 (1998)*.
Tibuleac et al., "Reflection and transmission guided-mode resonance filters", J. Opt. Soc. Am. A., vol. 14, No. 7, pp. 1617-1626 (1997)*.
Tibuleac et al., "Diffractive Narrow-Band Transmission Filters Based on Guided-Mode Resonance Effects in Thin-Film Multilayers", IEEE Photonics Technology Letters, vol. 9, No. 4, pp. 464-466 (1997)*.
Wawro, "Design, Fabrication and Testing of Waveguide Gratings for Spectral Filters, Photonic Antennas and Optical Fiber Sensors", Presentation, University of Texas at Arlington (1999)*.
Wawro et al., "Novel diffractive structures integrating waveguide-gratings on optical fiber endfaces", Presentation, Graduate Student Research Symposium (1999)*.
Tibuleac, "Guided-mode resonance reflection and transmission filters in the optical and microwave spectral ranges", Doctoral Dissertation Defense (1999)*.
Yariv, "Coupled-Mode Theory for Guided-Wave Optics", IEEE Journal of Quantum Electronics, vol. 9, No. 9, p. 919-933 (1973)*.
Wang et al., "Resonance of Asymmetric Dielectric Waveguides Containing a Diffraction Grating", IEEE (1990)*.
Hessel et al., "A New Theory of Wood's Anomalies on Optical Gratings", Applied Optics, vol. 4, No. 10, p. 1275-1299 (1965)*.
Lukosz et al., "Sensitivity of Integrated Optical Grating and Prism Couplers as (Bio)chemical Sensors", Sensors and Actuators, 15, p. 273-284 (1988)*.
Neviere et al., "About the Theory of Optical Grating Coupler-Waveguide Systems", Optics Communications, vol. 8, No. 2, p. 113-117 (1973)*.
Gaylord et al., "Analysis and Applications of Optical Diffraction by Gratings", IEEE, 73(5):894, p. 894-924 (1985)*.
Takada et al., "The integrins", Genome Biology, 8:215 (2007)*.
Sancho et al., "Binding kinetics of monomeric and aggregated IgG to Kupffer cells and hepatocytes of mice", Immunology, 53:283 (1984)*.

Chaplen et al., "Improvement of Bioactive Compound Classification through Integration of Orthogonal Cell-Based Biosensing Methods", Sensors, 7:38-51 (2007)*.

U.S. Appl. No. 13/073,233, filed Mar. 28, 2011*.

Reckless and Grainger, "Identification of oligopeptide sequences which inhibit migration induced by a wide range of chemokines", Biochem. J., 340:803-811 (1999).

Jackson et al., "Pharmacologic Actions of the Second-Generation Leukotriene B4 Receptor Antagonist LY293111: In Vitro Studies", The Journal of Pharmacology and Experimental Therapeutics, vol. 288, No. 1, 288:286-294 (1999).

Taguchi et al., "Patterns for RANTES Secretion and Intercellular Adhesion Molecule 1 Expression mediate Transephithelial T Cell Traffic Based on Analyses in Vitro and In Vivo", J. Exp. Med., vol. 187, No. 12, p. 1927-1940 (1998).

Dharmawardhane et al., "Localization of p21—Activated Kinase 1 (PAK1) to Pinocytic Vesciles and Cortical Actin Structures in Stimulated Cells", The Journal of Cell Biology, vol. 138, No. 6, p. 1265-1278 (1997).

Calderwood, "Integrin activation", Journal of Cell Science, 117:657-666 (2004).

Fleming et al., "PDE4—regulated cAMP degradation controls the assembly of integrin—dependent actin adhesion structures and REF52 cell migration", Journal of Cell Science, 117:2377-2388 (2004).

Mammoto et al., "Role of RhoA, mDia and Rock in cell Shape-dependent Control of the Skp2-p27(kip1) Pathway and the G1/S Transition", The Journal of Biological Chemistry, 279:26323-26330 (2004).

Desire et al., "RAC1 Inhibition Targets Amyloid Precursor Protein Processing by γ-Secretase and Decreases AB Production in Vitro and in Vivo", The Journal of Biological Chemistry, vol. 280, No. 45, p. 37516-37525 (2005).

Kim et al., "Chemokines: signal lamps for trafficking of T and B cells for development and effector function", Journal of Leukocyte Biology, 65:6-15 (1999).

Montresor et al., "Comparison Analysis of Normal versus CLL B-Lymphocytes Reveals Patient-Specific Variaiblity in Signaling Mechanisms Controlling LFA-1 Activation by Chemokines", Cancer Res. 69(24):9281-9290 (2009).

Pelish et al., "Secramine inhibits Cdc42-dependent functions in cells and Cdc42 activation in vitro", Nature Chemical Biology, 2:39-46 (2006).

Buckley et al., "Cell adhesion: more than just glue (Review)", Molecular Membrane Biology, 15:167-176 (1998).

Natsume et al., "Combination of Biomolecular Interaction Analysis and Mass Spectrometric Amino Acid Sequencing", Anal. Chem., 72:4193-4198 (2000).

HIGH RESOLUTION LABEL FREE ANALYSIS OF CELLULAR PROPERTIES

PRIORITY

This application is a continuation of U.S. Ser. No. 61/043,478, filed on Apr. 9, 2009, which claims the benefit of U.S. Ser. No. 61/043,478, filed on Apr. 9, 2008. These applications are incorporated herein by reference in their entirety.

BACKGROUND OF THE INVENTION

It has been estimated that at least two days of laboratory time and the use of fluorescent labels are required to assess cellular changes upon exposure to biological entities. See, e.g., Dharmawardhane et al., 1997, J. Cell Biol. 138(6):1265-78. Additionally, it has been estimated that at least 8-24 hours of laboratory time and the use of a secondary dye are required to quantify total cell movement or cell changes toward biological entities, such as a protein, peptide or small molecule. See, Reckless & Grainger. 1999. Biochem. J. 340: 803-811, Taguchi et al. 1998. J. Exp. Med. 187(12): 1927-1940, Jackson et al. 1999. J. Pharm. & Exper. Therapeutics. 288(1): 286-294 and Yarrow et al., 2004 BMC Biotechnol. 4(21):1-9. Methods are needed to reduce the time to perform these assays.

SUMMARY OF THE INVENTION

One embodiment of the invention provides a method of detecting a change in a cell growth pattern. The method comprises immobilizing one or more types of cells to a location on a surface of a colorimetric resonant reflectance optical biosensor with an antibody or a binding fragment thereof that specifically binds an adhesion protein; detecting a first colorimetric resonant reflectance optical peak wavelength value (PWV) for the location; incubating the one or more cells for a period of time or applying a test reagent to the one or more cells and incubating the one or more cells for a period of time; detecting a second colorimetric resonant reflectance optical PWV for the location; and comparing the first PWV to the second PWV. A difference between the first colorimetric resonant reflectance optical PWV in relation to the second colorimetric resonant reflectance optical PWV indicates a change in the cell growth pattern in the one or more cells. The change in cell growth pattern can be a change in cell morphology, change in cell adhesion, change in cell migration, change in cell proliferation, change in cell death, change in microtubule structure, change in microfilament structure, granule exocytosis, respiratory burst, cell differentiation, or a combination thereof. The PWVs can be detected using a scanner with a lens having a lower limit pixel size of about 1 micrometer to about 15 micrometers. The location on a surface of a colorimetric resonant reflectance optical biosensor can be an internal surface of a vessel selected from the group consisting of a microtiter well, microtiter plate, test tube, Petri dish, microfluidic channel, and microarray. The method can be completed in less than one hour.

Another embodiment of the invention provides a method of detecting a change in a cell growth pattern. The method comprises adding one or more types of cells to a colorimetric resonant reflectance optical biosensor, wherein one or more antibodies or a binding fragments thereof that specifically bind one or more adhesion proteins are immobilized on a location on the biosensor surface; optionally adding one or more adhesion proteins that specifically bind the one or more antibodies or binding fragments thereof to the biosensor surface; detecting a first colorimetric resonant reflectance optical peak wavelength value (PWV) for the location; incubating the one or more cells for a period of time or applying a test reagent to the one or more cells and incubating the one or more cells for a period of time; detecting a second PWV for the location; and comparing the first PWV and second PWV. A difference between the first PWV in relation to the second PWV indicates a change in the cell growth pattern in the one or more cells. The one or more cells can express an adhesion protein that specifically binds the one or more antibodies or binding fragments thereof. The one or more cells can express a receptor that specifically binds the one or more adhesion proteins.

Still another embodiment of the invention provides a method of detecting a change in a cell growth pattern. The method comprises adding one or more types of cells to a colorimetric resonant reflectance optical biosensor, wherein one or more antibodies or a binding fragments thereof that specifically bind one or more adhesion proteins are immobilized on a location on the biosensor surface; detecting colorimetric resonant reflectance optical peak wavelength values (PWVs) for the location over the whole time of the assay; optionally adding one or more adhesion proteins that specifically bind the one or more antibodies or binding fragments thereof to the biosensor surface; and incubating the one or more cells for a period of time or applying a test reagent to the one or more cells and incubating the one or more cells for a period of time. A difference between the PWVs over the time of the assay indicates a change in the cell growth pattern in the one or more cells.

DETAILED DESCRIPTION OF THE INVENTION

Figure 1A:
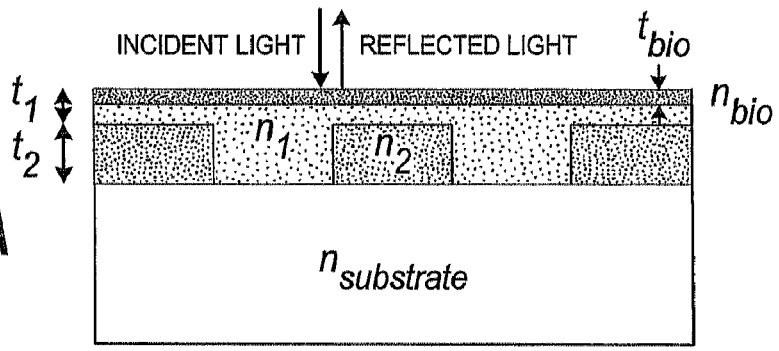
FIG. 1A shows a cross-sectional view of a colorimetric resonant reflectance biosensor wherein light is shown as illuminating the bottom of the biosensor; however, light can illuminate the biosensor from either the top or the bottom.

As used herein, the singular forms "a," "an", and "the" include plural referents unless the context clearly dictates otherwise.

One embodiment of the invention allows the direct detection of cell changes as they occur in real time with a colorimetric resonant reflectance biosensor and without the need to incorporate or without interference from radiometric, colorimetric, or fluorescent labels. Changes in cell behavior and morphology can be detected as the cell is perturbed. The cellular changes can then be detected in real time using a high speed, high resolution instrument, such as the BIND Scanner™ (i.e., a colorimetric resonant reflectance biosensor system), and corresponding algorithms to quantify data. See, e.g., U.S. Pat. No. 6,951,715 and U.S. Pat. Publ. 2004/0151626. By combining this methodology, instrumentation and computational analysis, cellular behavior can be expediently monitored in real time, in a label free manner.

Colorimetric resonant reflectance biosensors, such as SRU Biosystems, Inc. BIND™ technology (Woburn, Mass.) have the capability of measuring changes to a surface with respect to mass attachment from nanoscale biological systems. The applications and the methods, in which colorimetric resonant reflectance biosensors have been previously implemented, have changed as the resolution of the instruments has improved. Previously, measurement of the quantity of cells attached to the colorimetric resonant reflectance biosensor surface was the primary goal. While looking at some poorer resolution images of cells, however, it was noted that cells gave differential signals with respect to the number of pixels occupied, intensity of signal/pixel, change in PWV of each pixel, etc. While trying to reduce the variability of these data, it became clear that the variability lay within the individual cells and their differential morphological responses to stimuli. To further investigate these cellular events, a higher resolution version of a BIND Scanner™ (i.e., a colorimetric resonant reflectance biosensor system), was constructed. The scanner has a higher resolution lens than previously used scanners. The lens has a lower limit pixel size of about 7 micrometers. Additionally, a methodology was developed for analyzing cell changes in real time at better resolution.

Biosensors

Biosensors of the invention can be colorimetric resonant reflectance biosensors. See e.g., Cunningham et al., "Colorimetric resonant reflection as a direct biochemical assay technique," Sensors and Actuators B, Volume 81, p. 316-328, Jan. 5 2002; U.S. Pat. Publ. No. 2004/0091397. Colorimetric resonant biosensors are not surface plasmon resonant (SPR) biosensors. SPR biosensors have a thin metal layer, such as silver, gold, copper, aluminum, sodium, and indium. The metal must have conduction band electrons capable of resonating with light at a suitable wavelength. A SPR biosensor surface exposed to light must be pure metal. Oxides, sulfides and other films interfere with SPR. Colorimetric resonant biosensors do not have a metal layer, rather they have a dielectric coating of high refractive index material, such as $TiO_2$.

Grating-based waveguide biosensors are described in, e.g., U.S. Pat. No. 5,738,825. A grating-based waveguide biosensor comprises a waveguiding film and a diffraction grating that incouples an incident light field into the waveguiding film to generate a diffracted light field. A change in the effective refractive index of the waveguiding film is detected. Devices where the wave must be transported a significant distance within the device, such as grating-based waveguide biosensors, lack the spatial resolution of the current invention.

A colorimetric resonant reflectance biosensor allows biochemical interactions to be measured on the biosensor's surface without the use of fluorescent tags, colorimetric labels or any other type of detection tag or detection label. A biosensor surface contains an optical structure that, when illuminated with collimated and/or white light, is designed to reflect only a narrow band of wavelengths ("a resonant grating effect"). The narrow wavelength band (e.g., about 1 to about 10 nm) is described as a wavelength "peak." The "peak wavelength value" (PWV) changes when materials, such as biological materials, are deposited or removed from the biosensor surface. A readout instrument is used to illuminate distinct locations on a biosensor surface with collimated and/or white light, and to collect reflected light. The collected light is gathered into a wavelength spectrometer for determination of a PWV.

A biosensor can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment. Colorimetric resonant reflectance biosensors can also be incorporated into, e.g., microfluidic, macrofluidic, or microarray devices (see, e.g., U.S. Pat. Nos. 7,033,819, 7,033,821). Colorimetric resonant reflectance biosensors can be used with well-know methodology in the art (see, e.g., *Methods of Molecular Biology* edited by Jun-Lin Guan, Vol. 294, Humana Press, Totowa, N.J.) to monitor cell behavioral changes or the lack of these changes upon exposure to one or more extracellular reagents.

Colorimetric resonant reflectance biosensors comprise subwavelength structured surfaces (SWS) and are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. Propagation of guided modes in the lateral direction are not supported. Rather, the guided mode resonant effect occurs over a highly localized region of approximately 3 microns from the point that any photon enters the biosensor structure.

The reflected or transmitted light of a colorimetric resonant reflectance biosensor can be modulated by the addition of molecules such as specific binding substances or binding partners or both to the upper surface of the biosensor. The added molecules increase the optical path length of incident radiation through the structure, and thus modify the wavelength at which maximum reflectance or transmittance will occur.

In one embodiment, a colorimetric resonant reflectance biosensor, when illuminated with white and/or collimated light, is designed to reflect a single wavelength or a narrow band of wavelengths (a "resonant grating effect"). When mass is deposited on the surface of the biosensor, the reflected wavelength is shifted due to the change of the optical path of light that is shown on the biosensor.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates. A single spectrometer reading can be performed in several milliseconds, thus it is possible to quickly measure a large number of molecular interactions taking place in parallel upon a biosensor surface, and to monitor reaction kinetics in real time.

Figure 1B:
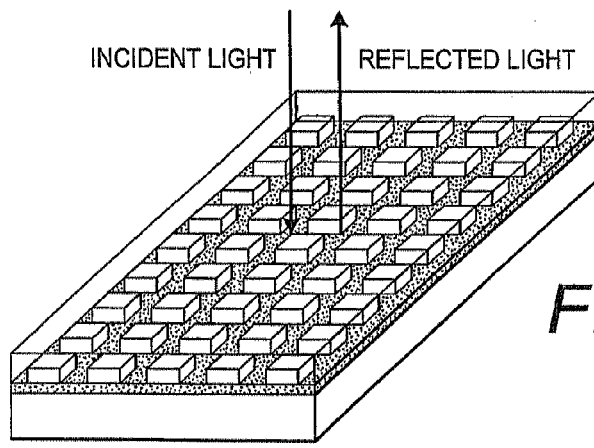
FIG. 1B shows a diagram of a colorimetric resonant reflectance biosensor wherein light is shown as illuminating the bottom of the biosensor; however, light can illuminate the biosensor from either the top or the bottom.

FIGS. 1A and 1B are diagrams of an example of a colorimetric resonant reflectance biosensor. In FIG. 1, $n_{substrate}$ represents a substrate material. $n_2$ represents the refractive index of an optical grating. $n_1$ represents an optional cover layer. $n_{bio}$ represents the refractive index of an optional biological material. $t_1$ represents the thickness of the optional cover layer above the one-, two- or three-dimensional grating structure. $t_2$ represents the thickness of the grating. $t_{bio}$ represents the thickness of the layer of the biological material. In one embodiment, are n2<n1 (see FIG. 1A). Layer thicknesses (i.e. cover layer, biological material, or an optical grating) are selected to achieve resonant wavelength sensitivity to additional molecules on the top surface. The grating period is selected to achieve resonance at a desired wavelength.

A colorimetric resonant reflectance biosensor comprises, e.g., an optical grating comprised of a high refractive index material, a substrate layer that supports the grating, and optionally one or more specific binding substances or linkers immobilized on the surface of the grating opposite of the substrate layer. The high refractive index material has a higher refractive index than a substrate layer. See, e.g., U.S. Pat. Nos. 7,094,595; 7,070,987. Optionally, a cover layer covers the grating surface. An optical grating is coated with a high refractive index dielectric film which can be comprised of a material that includes, for example, zinc sulfide, titanium dioxide, titanium oxide, titanium phosphate, tantalum oxide, silicon nitride, and silicon dioxide. A cross-sectional profile of a grating with optical features can comprise any periodically repeating function, for example, a "square-wave." An optical grating can also comprise a repeating pattern of shapes selected from the group consisting of lines (one-dimensional), squares, circles, ellipses, triangles, trapezoids, sinusoidal waves, ovals, rectangles, and hexagons. A colorimetric resonant reflectance biosensor of the invention can also comprise an optical grating comprised of, for example, plastic or epoxy, which is coated with a high refractive index material.

Figure 2:
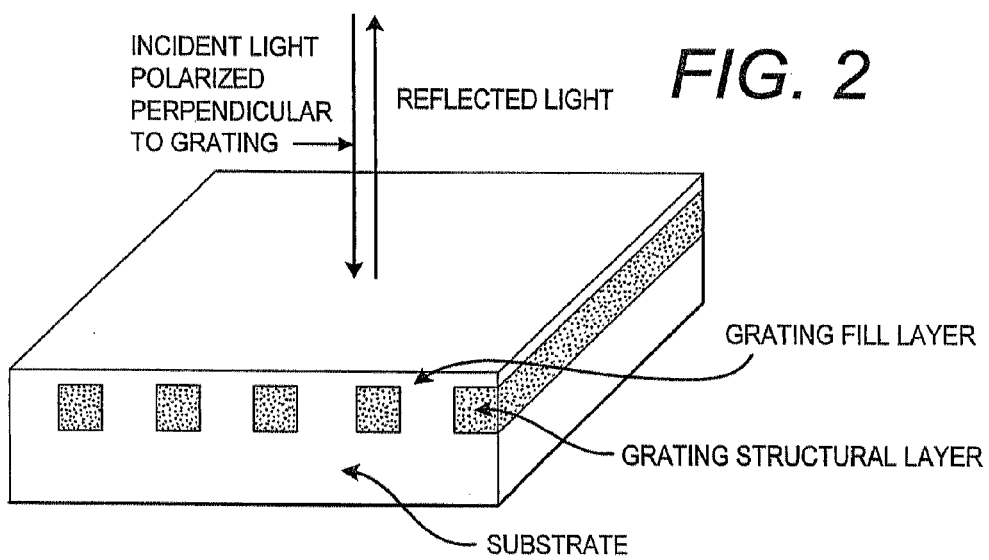
FIG. 2 shows an embodiment of a colorimetric resonant reflection biosensor comprising a one-dimensional grating.

Linear gratings (i.e., one dimensional gratings) have resonant characteristics where the illuminating light polarization is oriented perpendicular to the grating period. A schematic diagram of one embodiment a linear grating structure with an optional cover layer is shown in FIG. 2. A colorimetric resonant reflection biosensor can also comprise, for example, a two-dimensional grating, e.g., a hexagonal array of holes or squares. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

A colorimetric resonant reflectance biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a colorimetric resonant reflectance biosensor of the invention will be illuminated with white and/or collimated light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A detection system can comprise a colorimetric resonant reflectance biosensor a light source that directs light to the colorimetric resonant reflectance biosensor, and a detector that detects light reflected from the biosensor. In one embodiment, it is possible to simplify the readout instrumentation by the application of a filter so that only positive results over a determined threshold trigger a detection.

By measuring the shift in resonant wavelength at each distinct location of a colorimetric resonant reflectance biosensor of the invention, it is possible to determine which distinct locations have, e.g., biological material deposited on them. The extent of the shift can be used to determine, e.g., the amount of binding partners in a test sample and the chemical affinity between one or more specific binding substances and the binding partners of the test sample.

A colorimetric resonant reflectance biosensor can be illuminated twice. The first measurement determines the reflectance spectra of one or more distinct locations of a biosensor with, e.g., no biological material on the biosensor. The second measurement determines the reflectance spectra after, e.g., one or more cells are applied to a biosensor. The difference in peak wavelength between these two measurements is a measurement of the presence or amount of cells on the biosensor. This method of illumination can control for small imperfections in a surface of a biosensor that can result in regions with slight variations in the peak resonant wavelength. This method can also control for varying concentrations or density of cell matter on a biosensor.

Surface of Biosensor

One or more cells can be immobilized on a biosensor by for example, physical adsorption or by chemical binding. A cell can specifically bind to a biosensor surface via a specific binding substance such as a nucleic acid, peptide, an antibody or binding fragment thereof that specifically binds an adhesion protein, an adhesion protein, protein solution, peptide solution, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, virus, polymer or biological sample, wherein the specific binding substance is immobilized to the surface of the biosensor and the binding partner is on the surface of the cell.

Furthermore, cells can be arranged in an array of one or more distinct locations on the biosensor surface, said surface residing within one or more wells of a multiwell plate and comprising one or more surfaces of the multiwell plate or microarray. The array of cells comprises one or more cells on the biosensor surface within a microwell plate such that a surface contains one or more distinct locations, each with a different cell or with a different amount of cells. For example, an array can comprise 1, 10, 100, 1,000, 10,000 or 100,000 or greater distinct locations. Thus, each well of a multiwell plate or microarray can have within it an array of one or more distinct locations separate from the other wells of the multiwell plate, which allows multiple different samples to be processed on one multiwell plate. The array or arrays within any one well can be the same or different than the array or arrays found in any other microtiter wells of the same microtiter plate.

Immobilization of a cell to a biosensor surface can be also be affected via binding to, for example, the following functional linkers: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Furthermore, a cell can be immobilized on the surface of a biosensor via physical adsorption, chemical binding, electrochemical binding, electrostatic binding, hydrophobic binding or hydrophilic binding, and immunocapture methods.

In one embodiment of the invention a biosensor can be coated with a linker such as, e.g., a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. For example, an amine surface can be used to attach several types of linker molecules while an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Linkers and specific binding substances can be immobilized on the surface of a biosensor such that each well has the same linkers and/or specific binding substances immobilized therein. Alternatively, each well can contain a different combination of linkers and/or specific binding substances.

A cell can specifically or non-specifically bind to a linker or specific binding substance immobilized on the surface of a biosensor. Alternatively, the surface of the biosensor can have no linker or specific binding substance and a cell can bind to the biosensor surface non-specifically.

Immobilization of one or more specific binding substances or linker onto a biosensor is performed so that a specific binding substance or linker will not be washed away by rinsing procedures, and so that its binding to cells in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific cells can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Immobilization of specific binding substances to plastic, epoxy, or high refractive index material can be performed essentially as described for immobilization to glass. However, the acid wash step can be eliminated where such a treatment would damage the material to which the specific binding substances are immobilized.

Detecting Changes in Cell Growth Patterns or Cell Properties

It has been estimated that at least 8-24 hours of laboratory time and the use of a secondary dye are required to quantify total cell movement or cell changes in response to biological entities, such as a protein, peptide or small molecule. See, Reckless & Grainger. 1999. *Biochem. J.* 340: 803-811, Taguchi et al. 1998. *J. Exp. Med.* 187(12): 1927-1940, Jackson et al. 1999. *J. Pharm.& Exper. Therapeutics.* 288(1): 286-294 and Yarrow et al., 2004 *BMC Biotechnol.* 4(21):1-9; see also, U.S. Patent Appl. 2003/0068657, U.S. Patent Appl. 2003/0108954, U.S. Patent Appl. 2004/0091397, U.S. Patent Appl. 2005/0221271, U.S. Patent Appl. 2005/0074825, U.S. Patent Appl. 2005/0058639, U.S. Pat. Nos. 7,018,838, 6,982,171, and 5,601,997. The required amount of time for these types of assays can be reduced to a maximum of 3 hours or less using methods and compositions of the invention. For example, depending on the length of time cells are allowed to incubate on the surface of the biosensor, an assay can be completed in less than about 3 hours, 2 hours, 1 hour, 45 minutes, 30 minutes, 20 minutes, 10 minutes, 5 minutes or 3 minutes. Additionally, no dyes or detection labels are necessary.

With embodiments of the instant invention cell motility and changes in cell properties can be detected as it occurs, thus circumventing the need to incorporate detection labels such as radiometric, colorimetric, fluorescent labels or the need to use microscopy for evaluation. A colorimetric resonant reflectance biosensor detects directional cell movement and cell attachment as the cells transverse from an area containing no chemoattractant or protein to an area possessing an entity that induces cell motility. Analysis of cellular movement across a biosensor surface can be expediently monitored in real time, in a label free manner. Several other changes in cell growth patterns or other cell changes can be detected using the methods of this invention, such as change in cell morphology, change in cell adhesion, change in cell migration, change in chemotaxis or other cell movement, change in cell proliferation, change in microtubule structure, change in microfilament structure, granule exocytosis, respiratory burst, cell differentiation (e.g., neuronal elongation), fluctuations in adherence, morphological rearrangement, cytoskeletal rearrangement, cellular differentiation, apoptosis and cell death, change in cell absorption properties, cell signaling (e.g., GPCR/chemokine, RTK, ion channel) and protein secretion. A change in cell properties includes anything that changes a cell's size, shape, height and/or surface uniformity. The methods of the invention can also be used to monitor the reaction and response of cells to environmental or chemical stimuli. Cell movement, changes in cell growth patterns, and other cell responses or changes can be detected in real time using the BIND Biosensor™, BIND Reader™, and BIND Scanner™ (e.g., a colorimetric resonant reflectance biosensor system) and corresponding algorithms for quantification and analysis of data. See, e.g., U.S. Pat. No. 6,951,715, U.S. Patent Appl. Publ. 2004/0151626.

The BIND Biosensor™, BIND Reader™, and BIND Scanner™ (e.g., a colorimetric resonant reflectance biosensor system) and corresponding algorithms can be used to obtain high resolution cell images without the use labels and without killing the cells. High resolution images on the scale of about 1, 2, 3, 4, 5, 6, 7, 8, 9, 10, 50, 75, 100, 150, 175, 200, 300 µm or less can be obtained. Previous methods have employed wide-area or low resolution methods that provide essentially a bi-modal readout that provides little detailed information about the cells' mechanism of response. In contrast, the methods of the invention can provide micrometer resolution, and highly detailed information about a single cell, clusters of cells, or confluent populations of cells and any response the cells may have to stimuli. Wide area or low resolution methods of observing cells can require 10,000 to 60,000 cells in a standard 384 cell culture plate well. The high resolution methods of the invention, however, can provide information on less than 10,000 cells in a standard 384 cell culture plate well. For example, less than about 10, 100, 500, 1,000, 2,500, 5,000, 7,500, or 10,000 cells can be monitored using the methods of the invention. In one embodiment, a single cell can be monitored.

The high resolution, label-free signal provides great detail about cells on the surface of the biosensor. A signal may fall because the an area is experiencing a general reduction, may fall because some of the area is experiencing no reduction but a majority of the area is experiencing reduction, or the majority of the area is experiencing a major reduction while a small area is actually increasing in signal. The present invention allows the area being studied to fall within a cell such that focal adhesion points, cell morphology and the like are being determined on the single cell level so that the specific reason that a signal is falling or rising can be determined. Methods of the invention can even determine the strength of the cells' attachment to the biosensor. Therefore, the methods of the invention can provide information on the responses/changes within the cell or cells and can provide information as to the size of the area in which the cell or cells respond.

Methods of the invention are advantageous because they do not require fixing and/or staining of cells for microscopic or colorimetric/fluorimetric evaluation, they allow for continuous, multiple independent readings of the same population of cells in real time, they are quick, they require minimal reagent usage (both volume and type), and they do not require flowing the cells through a counting device. Additionally, the direction and velocity of cell movement or path can be determined in real time.

Methods of the invention allow for continuous monitoring or multiple independent readings of the same population of cells in real time over many days. Cellular changes can be quantified expediently and objectively over longer periods of time in a normal culturing environment (static with proper media). Methods of the invention can also be used synergistically with fluorescent labels to obtain additional, intracellular data from each cell or cell population.

Cell motility and cell properties can be monitored by taking a PWV for one location over several time periods. Alternatively, scans of a receptacle holding the cells, e.g., a microtiter plate well, can be done over several time periods. A receptacle refers to one container and not a collection of containers, e.g., a multiwell plate.

One or more cells can be applied to a location, such as a microtiter well on a surface of a colorimetric resonant reflectance optical biosensor. In one embodiment of the invention, one or more cells or one or more types of cells can be immobilized to a surface of the biosensor by an antibody (or a binding fragment thereof) that specifically binds an adhesion protein such as integrins, selectins, members of the IgSuperfamily, cadherins, syndecans, and ADAMs. See, e.g., Buckley et al., 1998, Mol. Memb. Biol. 15:167. An adhesion protein is located on a cell surface and is important in binding reactions with other cells and the extracellular matrix. A colorimetric resonant reflectance optical peak wavelength value (PWV) for the location is detected. The one or more cells can be incubated for a period of time (e.g., about 1 second, 30 seconds, 1, 2, 5, 10, 20, 30, 45 minutes, 1, 2, 5, 10 or more hours). Prior to the incubation, or after the incubation, or prior to the incubation and after the incubation one or more test reagents can be applied to the one or more cells. The colorimetric resonant reflectance optical PWV for the location can be detected for a second time. If a change in cell growth pattern or cell property occurs then the reflected wavelength of light is shifted as compared to a situation where no change occurs. The first PWV can be compared to the second PWV. A change in the PWV can indicate a change in cell growth pattern or cell properties in the one or more cells. PWVs over several time periods can be determined and compared. PWVs can also be monitored in real time over the entire time of the assay. For example, PWVs can be taken every second or fractions of seconds over the entire time of the assay. PWVs can also be taken every 5 seconds, 10 seconds, 30 seconds, minute, 5 minutes, 10 minutes or every hour over the course of the assay.

"Specifically binds" or "specific for" means that a first antigen, e.g., a polypeptide, recognizes and binds to an antibody with greater affinity than to other, non-specific molecules. A non-specific molecule is an antigen that shares no common epitope with the first antigen. For example, an antibody raised against an antigen (e.g., a polypeptide) to which it binds more efficiently than to a non-specific antigen can be described as specifically binding to the antigen. In one embodiment an antibody or antigen-binding portion thereof specifically binds to a polypeptide when it binds with a binding affinity about $K_a$ of $10^7$ l/mol or more. Specific binding can be tested using, for example, an enzyme-linked immunosorbant assay (ELISA), a radioimmunoassay (RIA), or a western blot assay using methodology well known in the art. Ligands and receptors can also specifically bind one another.

One or more antibodies (or binding fragments thereof) that specifically bind one or more adhesion proteins can be immobilized to the surface of the biosensor. One or more adhesion proteins can be added to the biosensor surface such that they are specifically bind to the immobilized antibodies. One or more types of cells are added to the surface of the biosensor before or after the addition of the adhesion proteins or at the same time the adhesion proteins are added to the biosensor surface. The cells can bind to the adhesion protein via a ligand that is specific for the adhesion protein. The adhesion protein can bind to the antibodies immobilized on the surface of the biosensor. Antibodies can directly bind adhesion proteins or antibodies can bind adhesion proteins through ligands fused or covalently or non-covalently bound to an adhesion protein. For example, the ZZ-binding domain of Protein A can be fused or bound to any adhesion protein. The adhesion protein can then bind IgG through the ZZ-binding domain of Protein A.

Figure 3:
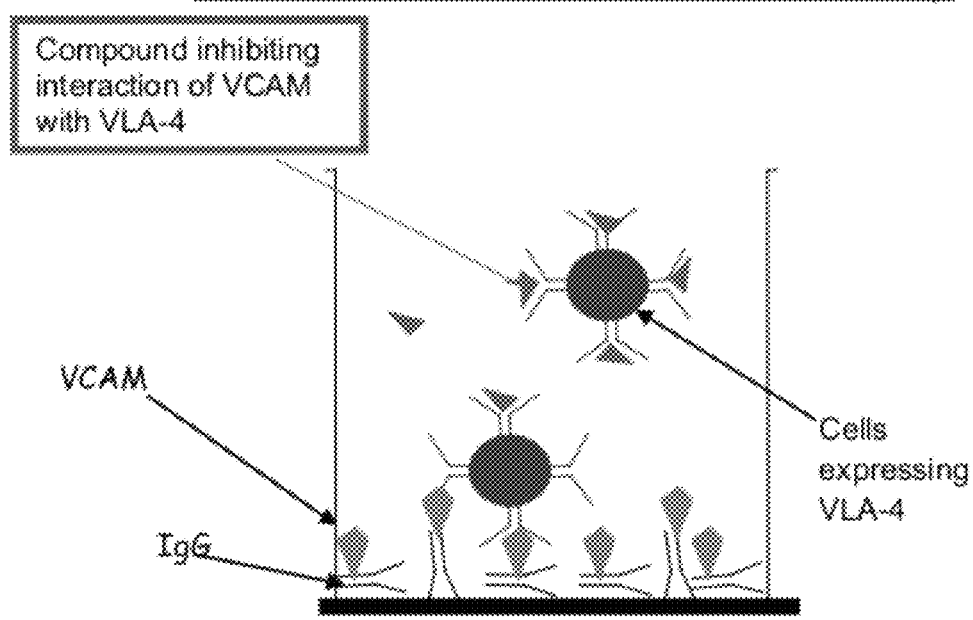
FIG. 3 shows a schematic diagram of a VLA-4 and VCAM-1 adhesion assay.

For example, VCAM-1 is an adhesion protein that is an endothelial ligand for VLA-4 and for integrin α4β7. VCAM-1 can be fused or bound to a ZZ-binding domain from Protein A. The ZZ-binding domain will specifically bind to IgG immobilized on the surface of the biosensor. Cells that express VLA-4 will bind to the VCAM-1 adhesion protein, which is bound to IgG immobilized to the surface of the biosensor. See FIG. 3. Therefore cells expressing an adhesion protein ligand will be immobilized to the biosensor surface.

Alternatively, one or more antibodies (or binding fragments thereof) that specifically bind one or more adhesion proteins can be immobilized to the surface of the biosensor. One or more types of cells that express the one or more adhesion proteins are added to the surface of the biosensor. The one or more adhesion proteins of the cells can bind to the immobilized one or more antibodies (or binding fragments thereof). Therefore, cells expressing adhesion proteins will be immobilized to the surface of the biosensor.

A test reagent can be, e.g., a metal ion such as Mn2+, Mg2+, or Ca2+, or a nucleic acid molecule, a polypeptide, an antigen, another cell type, an antibody fragment, a small organic molecule, or a small inorganic molecule. A small inorganic molecule or small organic molecule can be less than about 1, 5, 10, 50, 75, 100, 125, 150, 175, 200, 225, 250, 275 or 300 Da. Small organic or small inorganic molecules can be about 0.1 to about 500 Da, about 1 to about 300 Da, about 1 to about 200 Da, about 1 to about 100 Da, about 1 to about 50 Da, about 1 to about 25 Da, or any range in between about 0.1 to about 500 Da. A test reagent can also be a small molecule library, which can comprise about 5, 10, 25, 50, 100, 500, 1,000, 5,000, 10,000 or more different small molecules. Alternatively, a small molecule library can comprise only one type of small molecule. Cells can also be subjected to a change to a stimulus such as an environmental change (such as change in temperature, pressure or light).

Cells can respond to stimuli differently based upon what specific proteins or ligands the cell is bound. Therefore, the connections or binding events that the cell is actively involved in can affect how a cell will respond to stimuli such as test reagents or stimuli. The instant invention provides a method to simplify the connections or binding events the cell is experiencing during the assay. The only or one of the only binding events or connections the cell is making is between the cell receptor and adhesion protein that is bound to the one or more antibodies on the biosensor surface (or between a cell expressing an adhesion protein ligand and an adhesion protein that is bound to the one or more antibodies on the biosensor surface). Therefore, a more uniform response of the cell to stimuli or test reagents is expected.

Cell growth pattern or property changes at a biosensor location can be detected via the PWVs of the biosensor surface or monitored more generally using a microscope, digital camera, conventional camera, or other visualization apparatus, magnifying or non-magnifying, that utilizes lens-based optics or electronics-based charge coupled device (CCD) technology.

Preferably, the resolution of the lens of the scanner determining the PWV has an about 1, 2, 4, 5, 6, 7, 8, 9, 10, 11, 12, 13, 14, 15, 16, 17, 18, 19, or 20 micrometer pixel size. Previous scanners had a pixel size of greater than about 20 micrometers. Assays of the invention can be completed in less than 1, 2, 3, 4, 5, 6, 7, or 8 hours. That is, cell changes in response to, for example, and added reagent can be determined in a time efficient manner.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims. In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Figure 4:
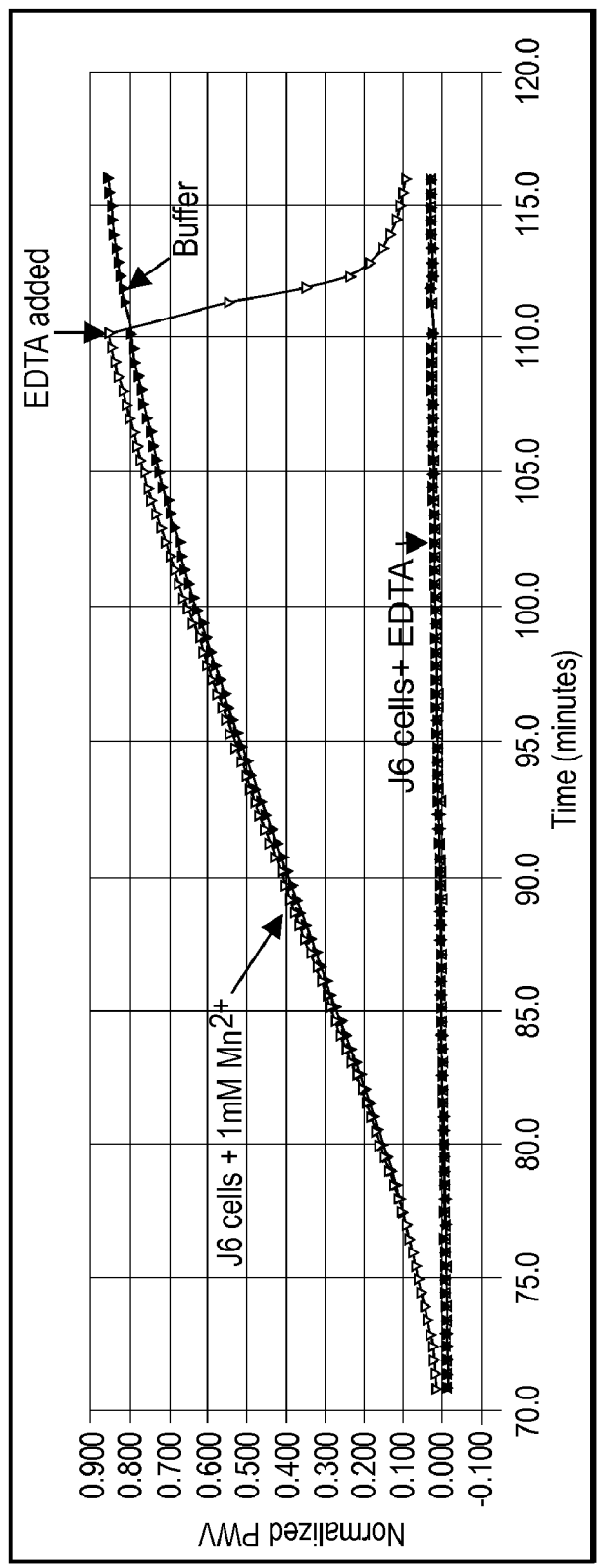
FIG. 4 shows the results from a VLA-4 and VCAM-1 adhesion assay.

VCAM-1, which was fused to the ZZ-binding domain of Protein A, was added to a biosensor having IgG immobilized to its surface. J6 cells, which express VLA-4, were added to the biosensor surface. FIG. 4 shows normalized PWVs over time for J6 cells that were added to the biosensor. The "J6 cells+1 mM $Mn^{2+}$" and "Buffer" lines shown in FIG. 4 both contained J6 cells and 1 mM $Mn^{2+}$. The "J6 cells and EDTA" line contained J6 cells and EDTA. At the 110 minute mark, EDTA was added to the "J6 cells+1 mM $Mn^{2+}$" cells. The amount of binding of cells to the VCAM-1 immobilized to the surface of the biosensor quickly dropped off because EDTA inhibits the ability of $Mn^{2+}$ to mediate VCAM-1 and VLA-4 binding. The results in FIG. 4 demonstrate that the PWV changes and therefore cell binding changes are indeed due to changes in VLA-4 and VCAM-1 binding.

We claim:

1. A method of detecting a change in a cell growth pattern comprising:
   a) adding one or more B-cells to a colorimetric resonant reflectance optical biosensor, wherein one or more one or more adhesion proteins are immobilized on a location on the biosensor surface, and wherein the one or more B-cells express a receptor that specifically binds the one or more adhesion proteins;
   c) detecting a first colorimetric resonant reflectance optical peak wavelength value (PWV) for the location;
   d) applying one or more test reagents to the one or more B-cells and incubating the one or more cells for a period of time;
   e) detecting a second PWV for the location; and
   f) comparing the first PWV and second PWV;
   wherein a difference between the first PWV in relation to the second PWV indicates a change in the cell growth pattern in the one or more B-cells.

2. The method of claim 1, wherein the one or more adhesion proteins are VCAM-1 or ICAM-1.

3. The method of claim 1, wherein the one or more B-cells are activated with IgM prior to step d).

4. The method of claim 1, wherein the change in cell growth pattern is protein secretion.

5. The method of claim 1 wherein the change in cell growth pattern is a change in cell morphology, change in cell adhesion, change in cell migration, change in cell proliferation, change in cell death, change in microtubule structure, change in microfilament structure, granule exocytosis, respiratory burst, cell differentiation, or a combination thereof.

6. The method of claim 1, wherein the PWV is detected using a scanner with a lens having a lower limit pixel size of about 1 micrometers to about 15 micrometers.

7. The method of claim 1, wherein the location on a surface of a colorimetric resonant reflectance optical biosensor is an internal surface of a vessel selected from the group consisting of a microtiter well, microtiter plate, test tube, Petri dish, microfluidic channel, and microarray.

8. The method of claim 1, wherein the method is completed in less than one hour.

9. The method of claim 1 wherein the change in cell growth pattern is a change in cell adhesion.

\* \* \* \* \*